United States Patent [19]

Woo

[11] Patent Number: 4,514,461
[45] Date of Patent: Apr. 30, 1985

[54] FRAGRANCE IMPREGNATED FABRIC

[76] Inventor: Yen-Kong Woo, 1545 Geary Blvd., San Francisco, Calif. 94115

[21] Appl. No.: 291,443

[22] Filed: Aug. 10, 1981

Related U.S. Application Data

[63] Continuation-in-part of Ser. No. 130,728, Mar. 17, 1980, abandoned.

[51] Int. Cl.³ .............................................. B32B 5/16
[52] U.S. Cl. .................................... 428/240; 428/280; 428/290; 428/321.5; 428/323; 428/905
[58] Field of Search ............... 428/245, 283, 290, 240, 428/321.5, 905, 323, 325, 327; 401/132; 424/16, 27, 31, 76; 252/316

[56] References Cited

U.S. PATENT DOCUMENTS

| | | | |
|---|---|---|---|
| 3,137,631 | 6/1964 | Soloway | 424/16 |
| 3,565,753 | 2/1971 | Yurkowitz | 428/905 |
| 4,145,184 | 3/1979 | Brain | 428/905 |
| 4,254,179 | 3/1981 | Carson et al. | 428/905 |

*Primary Examiner*—Paul J. Thibodeau
*Attorney, Agent, or Firm*—Alfons Puishes

[57] ABSTRACT

This invention is a fabric impregnated with micron-size bubbles in the form of fragile capsules within the interstices between the strands inside the body of the fabric by spraying the capsules in combination with a liquid binder and then putting the fabric through a set of rollers, the invention being that the micron-size bubbles are so bonded completely within the interior of the fabric that when rubbed, certain of the bubbles break and release the fragrance from the broken capsules, none of the capsules being on the outside of the fabric surface.

1 Claim, 2 Drawing Figures

FRAGRANCE IMPREGNATED FABRIC

This application is a continuation-in-part of my co-pending application Ser. No. 06/130,728 filed March 17, 1980 abandoned.

BACKGROUND OF THE INVENTION

Process of coating certain materials, such as the surface of paper, is old in the art. The micropackaging technique is a process applying a thin polymeric coating on the surface of materials with the content being the desired fragrance.

It is known that perfume makers introduced perfume into printing ink for readers to sniff such as perfumed advertisements.

Microencapsulation is a well known micro-packaging technique which involves deposition of thin polymeric coatings to minute particles of solids, droplets of liquids, or dispersions of solids in liquids. Such capsules have been used in the pharmaceutical industry and industrial chemicals.

There are several processes for coating minute particles employing the principles and phenomenon of coacervation. This is a generalized phase separation phenomenon involving the emergence from a homogenous solution of polymeric material liquid droplets of concentrated solution rather than solid aggregates. Such separated emergent phase in the form of amorphous, liquid drops, constitutes the coacervate. Deposition of this coacervate around individual minute insoluble particles dispersed in the equilibrium liquid form embryonic capsules, and appropriate gelling of the coacervate deposits results in useful microcapsules, with or without after-treatment to modify the properties of the containing polymeric wall.

Such processes are described in U.S. Pat. No. 3,137,631 to Soloway which also discloses a fibrous tissue or paper containing such capsules. Additional processes are described in U.S. Pat. No. 4,087,376 and U.S. Pat. No. 4,100,103 to Foris, et al.

U.S. Pat. No. 3,145,184 to Brain teaches a method of entraining microcapsules in fabric by mixing them with laundry detergents and then washing the fabric which does not insure uniform and firm impregnation of the fabric.

U.S. Pat. No. 3,640,629 to Geiser discloses a tape or narrow strip of sheet material having rupturable microcapsules entrapped on its surface.

U.S. Pat. No. 4,201,822 to Cowsar teaches a fabric in which a resin finish is used on the fabric to contain decontamination agents for reaction with toxic substances. No novel method of impregnation is disclosed.

SUMMARY OF THE INVENTION

The novelty of the present invention is impregnating fabric with microcapsules, the core of each of which is an essential oil suitable to function as a deodorant or the like. The essence is encapsulated in impervious waterproof polymer container of micron-size, wherein the container wall is sufficiently fragile to break upon rubbing under pressure thereby to release the fragrance of the encapsulated core.

It is an essential part of the invention that this encapsulated essential oil substance be not spread as a coating on the surface of some material porous or otherwise. But on the contrary, the encapsulated micron-sized bubbles are imbedded completely within the interstices between the strands of the fabric so that they remain within the fabric and are practically invisible on the surface of the fabric and do not vary the appearance or feel of the fabric surface.

The capsules are sprayed into the fabric or saturated in a solution of binder and the fabric then rolled between two heated rollers with equal pressure and temperature to insure deep and uniform penetration.

DETAILED DESCRIPTION

Figure 1:
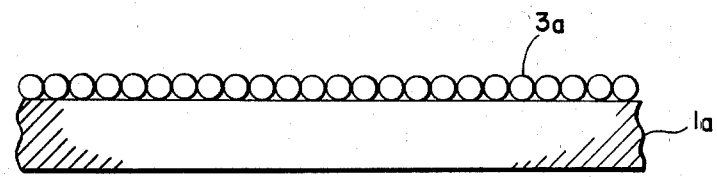
FIG. 1 illustrates surface on a much enlarged coated paper or the like which represents prior art.
Figure 2:
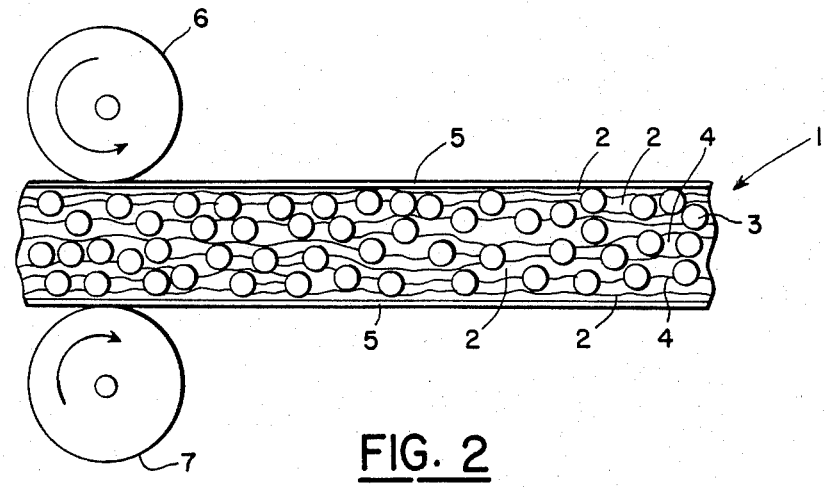
FIG. 2 illustrates a much enlarged scale, the fabric impregnated according to this invention and diagrammatic representation of the rollers used to complete the process, with equal degree of high heat and pressure.

The fabric 1 woven, non-woven or otherwise made, has strands 2 therein which form the fabric body. The micron binder coated capsules 3 in the form of minute bubbles are confined in the interstices 4 around the strands of the fabric. On account of the extremely and relatively small size of the capsules, the general texture and feel of the fabric is not altered. The outer surfaces 5 of the fabric are smooth and capsule free.

The polymer container walls of the bubbles are of sufficient fragility to break upon rubbing between the fingers or otherwise with normal hand pressure and the liberated core provide the fragrance for deodorization, disinfectant and the like to suit the needs of the user.

On FIG. 1, 3a shows capsules on surface 1a in prior art.

The deodorizer fabric may be then manufactured into any shape or size as necessary, for instance, as into fabric handled in the usual manner and which can be sewed into medical supplies, coats, jackets, ties, handbags, belts, pillows, cushions, stuffed toys, decorations and the like, and the deodorizer fragrance or disinfectant remains concealed within the fabric unnoticeably.

It is important that the encapsulated fragrant substance is in such minute bubbles as to be of substantially dust consistency in bulk. These microbubbles or capsules are impregnated in the fabrics, such as cotton, wool, silk, or synthetic fabrics, by any known microbinding process and agents.

The herein impregnated fabric is an important advancement over the previous "scratch and sniff" products of former years, and over the surface coated paper products as shown in FIG. 1, because immensely larger quantities of capsules are contained in the substrate of the fabric and the fragrance lasts much longer than said previous products. The resulting fabric has greater durability, convenience and inconspciuousness. It can have a selection of deodorant, hygienic disinfectant or other fragrances and the fabric may be dyed with any desired color.

Important advantages of the herein described fabric are: lasting quality because the unbroken capsules remain effective and are not subject to deterioration such as dripping or molding or drying out or straining; the elimination of presently used bulky containers and dispensers; and the selective adjustability of the strength of fragrance released by fragmenting less or more of the bubbles.

I utilize a liquid acrylic latex of any known formula for the capsules as a binder which I spray or saturate into the fabric so that the capsules 3 are binder coated and imbedded in the interstices 4. I then dry and press the fabric between equally heated rollers 6 and 7 at a temperature of approximately 300° plus Fahrenheit and just enough pressure to insure driving the capsules firmly into the fabric and not rupturing them. The rollers are kept at the same temperature and pressure to insure uniformity. Since all capsules are firmly positioned in the fabric it can stand laundering as I have verified by test.

I claim:

1. A fabric having an impregnation of micro-sized capsules;

said capsules being formed by a fragrance emitting core encapsules in a micro-sized container of sufficient strength to resist breakage under normal handling of the fabric but sufficiently fragile to rupture under suitably exerted hand pressure to release said fragrance;

said impregnation having the characteristic of being sprayed with said capsules in company with a liquid binder by a forceful spray to insure complete and uniform penetration of said fabric by said capsules;

said fabric having the characteristic of having passed lightly between heated pressure rollers to insure absence of any capsules on its surface thus providing a smooth surface on said fabric.

* * * * *